United States Patent
Kasper et al.

(10) Patent No.: US 10,605,802 B2
(45) Date of Patent: Mar. 31, 2020

(54) UNIVERSAL SOLVENT INDICATING SYSTEM

(71) Applicant: Brady Worldwide, Inc., Milwaukee, WI (US)

(72) Inventors: Matthew Kasper, Oak Creek, WI (US); Michael Labelle, Hubertus, WI (US); Nicholas Krogman, Hubertus, WI (US); Bethany Grillo, Champaign, IL (US)

(73) Assignee: Brady Worldwide, Inc., Milwaukee, WI (US)

( * ) Notice: Subject to any disclaimer, the term of this patent is extended or adjusted under 35 U.S.C. 154(b) by 200 days.

(21) Appl. No.: 15/589,727

(22) Filed: May 8, 2017

(65) Prior Publication Data

US 2017/0254802 A1    Sep. 7, 2017

Related U.S. Application Data

(63) Continuation-in-part of application No. PCT/US2015/031735, filed on May 20, 2015.

(51) Int. Cl.
*G01N 33/00* (2006.01)
*G01N 33/52* (2006.01)
*G01N 31/22* (2006.01)

(52) U.S. Cl.
CPC .......... *G01N 33/525* (2013.01); *G01N 31/22* (2013.01)

(58) Field of Classification Search
CPC .................................................. G01N 33/525
USPC ......................................................... 436/170
See application file for complete search history.

(56) References Cited

U.S. PATENT DOCUMENTS

| | | | |
|---|---|---|---|
| 2005/0118415 A1* | 6/2005 | LaBrosse | B32B 7/12 428/349 |
| 2008/0145611 A1 | 6/2008 | Mess et al. | |
| 2012/0062893 A1* | 3/2012 | Rakow | G01N 21/78 356/405 |
| 2012/0067270 A1 | 3/2012 | Huynh | |
| 2014/0224170 A1 | 8/2014 | Noe | |

OTHER PUBLICATIONS

PCT International Search Report and Written Opinion from corresponding International Application No. PCT/US2015/031735, dated Aug. 17, 2015, 11 pages.

* cited by examiner

*Primary Examiner* — Christopher Adam Hixson
*Assistant Examiner* — Emily R. Berkeley
(74) *Attorney, Agent, or Firm* — Quarles & Brady LLP

(57) ABSTRACT

A saturation indication system includes a sorbent body with a film backing being irreversibly bonded to the sorbent body. A universal indicating ink formulation is at least partially coated onto the film backing such that the ink formulation is disposed between the film backing and the sorbent body. The universal indicating ink formulation includes a resin and a dye dispersed in the resin. The dye is configured to indicate a state of saturation of the sorbent body, with the resin and the dye being soluble in a plurality of categories of sorbates consisting of hydrophobic sorbates, hydrophilic sorbates, neutral sorbates, and amphiphilic sorbates.

20 Claims, 4 Drawing Sheets

UNIVERSAL SOLVENT INDICATING SYSTEM

CROSS-REFERENCE TO RELATED APPLICATION

This application is a continuation-in-part application of PCT International Application No. PCT/US2015/031735 filed on May 20, 2015, the contents of which are incorporated by reference for all purposes as if set forth in its entirety.

FIELD OF INVENTION

This disclosure relates to sorbent products and, more particularly, to sorbent products with saturation indicators that are capable of identifying multiple different types of solvents.

BACKGROUND

Sorbent products such as mats, wipes, socks, and booms are commonly used to absorb fluids. These sorbent products are frequently used in industrial facilities and may be placed in an area where a leak or spill is occurring or may be anticipated. For example, sorbent products can be placed around equipment or attached to equipment or pipes. Apart from the industrial applications, sorbent products are also applicable for cleaning up more routine spills in facilities like grocery stores, hospitals, and schools.

Melt-blown polypropylene (MBPP) sorbents are widely used as they are durable, inexpensive and readily collect liquid spills. Compared to alternatives, such as clay granules, MBPP sorbents are clean (e.g., non-dusting) and easy to use. MBPP sorbents without further modifying additives are naturally oleophilic, meaning that they attract non-polar liquids including most oils, while rejecting polar solvents including water. However, MBPP sorbents can also be modified to attract both polar and non-polar liquids, often called "universal" sorbents. For example, MBPP sorbents can be made to attract oil and water by adding a surfactant during the manufacturing process. Thus, MBPP is a particularly versatile sorbent material.

However, during use, sorbent products will reach a point of saturation which causes the sorbent material to become non-effective. Accordingly, the user of a sorbent product often must remove the sorbent product from the application or use site in order to ascertain whether the sorbent product has reached its saturation capacity. This process is inconvenient to the user and sometimes causes a delay in replacing the sorbent product even once it has passed its point of saturation. Additionally, this process increases costs associated with the sorbent product. Additional labor costs are necessary to remove, check, and replace a sorbent product that is less than fully saturated. Also, if the sorbent product is discarded prior to achieving full saturation, additional costs are incurred when putting into place new sorbent products prematurely.

U.S. Pat. No. 7,892,639 to Brady Worldwide, Inc., which is incorporated by reference herein in its entirety for all purposes, discloses an edge ingress label for attachment to a surface. This label includes one or more ink formulations which are dissolvable and dispersible within the label to visually indicate the presence of the solvent in the label.

SUMMARY

Systems such as that disclosed in U.S. Pat. No. 7,892,639 are typically engineered to work with one type or class of solvent and includes either water-soluble components or organic solvent-soluble components. Put more simply, these detection systems are designed to detect either water or oils, but not both.

Disclosed herein is a universal solvent indicating system that is able to detect multiple classes of solvents including, for example, water and oils using a single universal ink formulation that is dissolvable when placed in contact with either water or oil. In contrast, to date, most systems were able to detect one class of solvents, but not another.

According to one aspect of the invention, a saturation indication system includes a sorbent body, a film backing, and a universal indicating ink formulation. The sorbent body has an upper surface and a lower surface and the sorbent body is configured to absorb a sorbate. The film backing is irreversibly bonded to the lower surface of the sorbent body. The universal indicating ink formulation is partially coated onto the film backing such that the universal indicating ink formulation is disposed between the film backing and the sorbent body. The universal indicating ink formulation includes a resin and a dye dispersed in the resin in which the dye is configured to indicate a state of saturation of the sorbent body. The resin and the dye are soluble in a plurality of categories of sorbates consisting of hydrophobic sorbates, hydrophilic sorbates, neutral sorbates, and amphiphilic sorbates.

In some forms, the dye may be stationary within the resin before the sorbate saturates the resin of the universal indicating ink formulation, the dye may disperse into the sorbent body after the sorbate saturates the resin, and the dispersion of the dye may be indicative that the resin has been contacted by the sorbate.

In some forms, the sorbent body may be a meltblown polypropylene sorbent pad and the film may be a spunbond polypropylene film integrated into the meltblown polypropylene sorbent pad. The spunbond polypropylene film may be integrated into the meltblown polypropylene sorbent pad by bonding them together via ultrasonic welding.

In some forms, the saturation indication system may further include a covering ply coupled to one of the upper surface and the lower surface of the sorbent body, opposite the surface receiving the film backing. The covering ply may be a spunbond polypropylene layer ultrasonically welded to the upper surface of the sorbent body.

In some forms, the saturation indication system may further include a nonskid film coupled to the film backing, opposite the side of the film backing attached to the sorbent body. The nonskid film may provide a non-permeable barrier inhibiting transport of the sorbate through the non-permeable barrier.

In some forms, the film backing may be irreversibly bonded to the lower surface of the sorbent body. The film backing may cover a portion of a surface area of the lower surface of the sorbent body.

In some forms, the resin may be made of at least one of acrylic, polyesters, rubbers, latexes, silicones, and styrene copolymers and the dye may be at least one of anthracene, azo, anthraquinone, pyrazolone, and quinine dye. In some forms, the resin may be opaque.

In some forms, the sorbent body may provide an opaque layer disposed above the universal indicating ink formulation to conceal the universal indicating ink formulation before the dye is dispersed into the sorbent body.

In one particular forms, the universal indicating ink formulation may contain 20 parts dye, 10 parts resin, 68.4 parts solvent, and 1.6 parts additive. The 20 parts dye may include 10 parts Red 2214 (Acid Red 1) and 10 parts Red 7335 (Solvent Red 24), the resin may include a styrene acrylic copolymer, the 68.4 parts of solvent may include 34.2 parts n-butyl acetate and 34.2 parts toluene, and the 1.6 parts additive may include a hydroxyl functional carboxylic acid ester.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

BRIEF DESCRIPTION OF THE DRAWINGS

The present invention will hereafter be described with reference to the accompanying drawings, wherein like reference numerals denote like elements.

DETAILED DESCRIPTION

A saturation indicator for indicating saturation of a sorbent product by a sorbate is disclosed herein. The term "sorbent body" refers hereinafter to any absorbent material in any form which can absorb a fluid.

The sorbent body may be a melt-blown polypropylene (MBPP) sorbent. For example, the sorbent body may be a MBPP mat made of non-woven polypropylene fibers, intended as a sorbent for oil or liquid-based spills. The mat may be used to clean or contain spills on floors, for example. Alternatively, the sorbent body may be made of hygroscopic material, acetobacteria, cotton wool, minerals, wood with high percentage of cellulose, and polymers. Suitable structures for the sorbent body include, but are not limited to, mats, wipes, socks, booms, and the mixtures thereof.

The term "saturation" or "pre-determined saturation threshold" refers hereinafter to a predetermined relative degree of saturation that is less or equal to the absolute degree of saturation by a sorbate to be absorbed by the sorbent product. For example, the threshold of saturation can be about 10%, 20%, 30%, 40%, 50%, 60%, 70%, 80%, 90%, or 100% of the saturation capacity of the sorbent body. Preferably, the threshold of saturation is at least 80%, or more preferably at least 90%, of the saturation capacity of the sorbent body.

The term "saturation indicator" refers hereinafter to a mechanism or a device that is configured to inform a user of a state of saturation of the sorbent body. The saturation indicator further informs the user when the pre-determined threshold of saturation has been met. The information provided by the saturation indicator to the user can be in any form that is visual to the user.

Figure 1B:
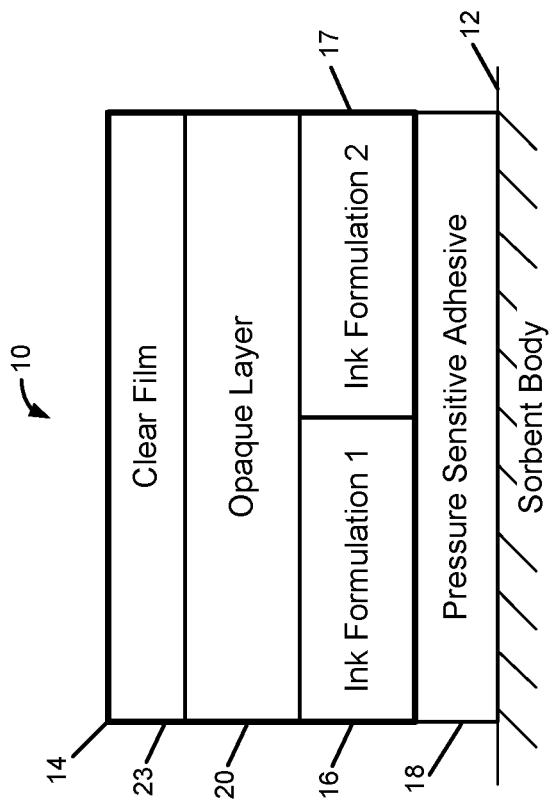
FIG. 1B is a second embodiment of a saturation indicator in contact with a sorbent body in which the saturation indicator has multiple ink formulations.
Figure 1A:
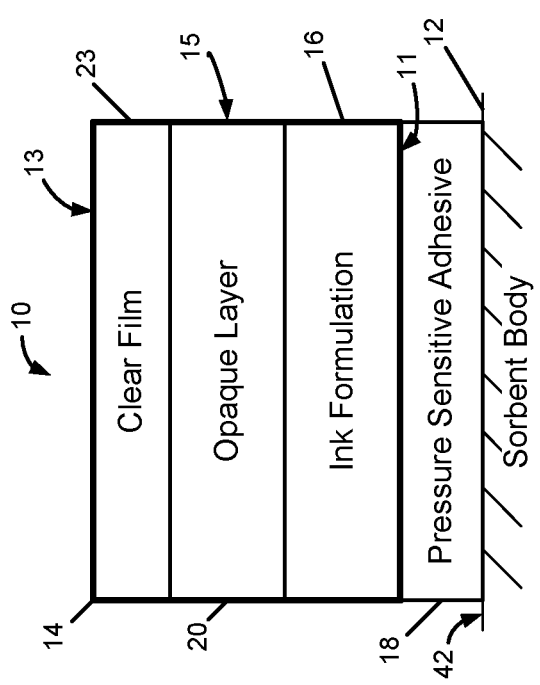
FIG. 1A is a first embodiment of a saturation indicator in contact with a sorbent body.

Referring first to FIG. 1A, an embodiment of the saturation indicator 10 is shown in which the saturation indicator 10 disposed on an upper surface 42 of a sorbent body 12. The saturation indicator 10 includes a label body 14 that supports a universal indicating ink formulation 16. The universal indicating ink formulation 16 includes a suspension of a resin and a dye dispersed within the resin. The resin may be, for example, an acrylate resin, a styrene-isopene copolymer, a rubber-based resin, or the like.

A pressure sensitive adhesive (hereinafter, "PSA") 18 is disposed on a lower surface 11 of the label body 14 and is used to form a bond between the label body 14 and the sorbent body 12. This PSA 18 can either be unsupported (that is, have no film barrier between an absorbing material layer such as that illustrated in FIGS. 2A and 2B and the PSA), or more preferably be a supported adhesive (that is, have a film barrier between an absorbing material layer or the label body and the PSA). The PSA 18 may alternatively be disposed on another surface of the label body 14, for example an upper surface 13 or an edge or side surface 15 depending on the particular configuration for attachment. In the particular form illustrated, the PSA 18 being disposed on the lower surface 11 of the label body 14 permits the label to act as an edge ingress label.

While the bond between the label body 14 and the sorbent body 12 is referenced throughout the application as a PSA, those skilled in the art will recognize that alternative ways of integrating the label or saturation indicator onto the sorbent body are possible, for example a hook, a thread, or a fusion point.

The dye and the resin of the universal indicating ink formulation 16 are soluble when exposed to a sorbate from the sorbent body 12. It should be appreciated that the sorbent body 12 is configured to absorb the sorbate and, when the sorbent body 12 is saturated to at least a pre-determined threshold, some amount of sorbate will be introduced to the saturation indicator 10 via the edges 15 of the saturation indicator 10. Examples of the dye include, but are not limited to, antracene, azo, antraquinone, pyrazolone, quinine dye, and the mixtures thereof. In one example, the dye is a mixture of hydrophobic soluble and hydrophilic soluble dyes.

The sorbate absorbed by the sorbent body 12 can be selected from the group of categories of sorbates consisting of hydrophobic sorbates, hydrophilic sorbates, neutral sorbates, and amphiphilic sorbates. The universal indicating ink formulation 16 is configured to be soluble in a plurality of sorbates selected from the aforementioned group of sorbates. For example, the universal indicating ink formulation 16 may be soluble in both hydrophobic and hydrophilic solvents or sorbates. In contrast, prior systems might have provided ink formulations that were soluble in hydrophobic solvents or sorbates, but not in hydrophilic solvents or sorbates (or vise-versa).

Prior to contact with the solvent or sorbate, the dye of the universal indicating ink formulation 16 is initially stationary within the resin before the sorbate flows from the sorbent body 12 into the label body 14. Indeed, the PSA 18 may be configured to provide a non-permeable barrier which inhibits flow of the sorbate from the sorbent body 12 into the label body 14 until some amount of saturation is exceeded in the sorbent body 12, such that the sorbate flows around the PSA 18 to enter the label body 14 from the edges 15. The saturation indicator 10 may therefore be an edge-ingress indicator, in which the sorbate flows around the PSA 18 to enter the label body 14 through the side surface 15 of the label body 14. At least in the form illustrated in FIGS. 1A and 1B, when the dye is released, it may migrate onto the upper surface 42 of the sorbent body 12.

The label body 14 may further include an opaque layer 20, for example a cross-linked resin such as acrylate with a dispersed pigment, disposed above the universal indicating ink formulation 16. The opaque layer 20 can be configured to inhibit a user from viewing the dye within the universal indicating ink formulation 16 when the dye is still contained within the resin in the label body 14. The label body 14 can also include a clear film 22, for example polyethylene terephthalate (PET), disposed above the opaque layer 20. The clear film 22 does not need to be PET, but if present, can be somewhat clear to permit observation of the indicating dye by the user (although this viewing is more significant in the embodiments illustrated in FIGS. 2A and 2B in which there is an absorbing material into which the dye migrates). While the opaque layer 20 is illustrated in FIG. 1A as entirely covering the ink formulation 16, different covering patterns can be employed such as, for example, those illustrated in FIG. 2A, 2B, or 3.

As shown in FIG. 1B, the label body 14 may further include a second indicating ink formulation 17. The second indicating ink formulation 17 may include a second dye and a second resin, and may be configured to be soluble in a second sorbate (or second plurality of sorbates to provide a second group of sorbates for indication) which is at least partially different than the sorbates in the first plurality of sorbates in which the universal indicating ink formulation 16 is soluble. The second sorbate may be selected from the aforementioned group of sorbates (or may include a second plurality of sorbates). In this way, multiple ink formulations may be provided in a single label that detect or indicate different sorbates.

Figure 2A:
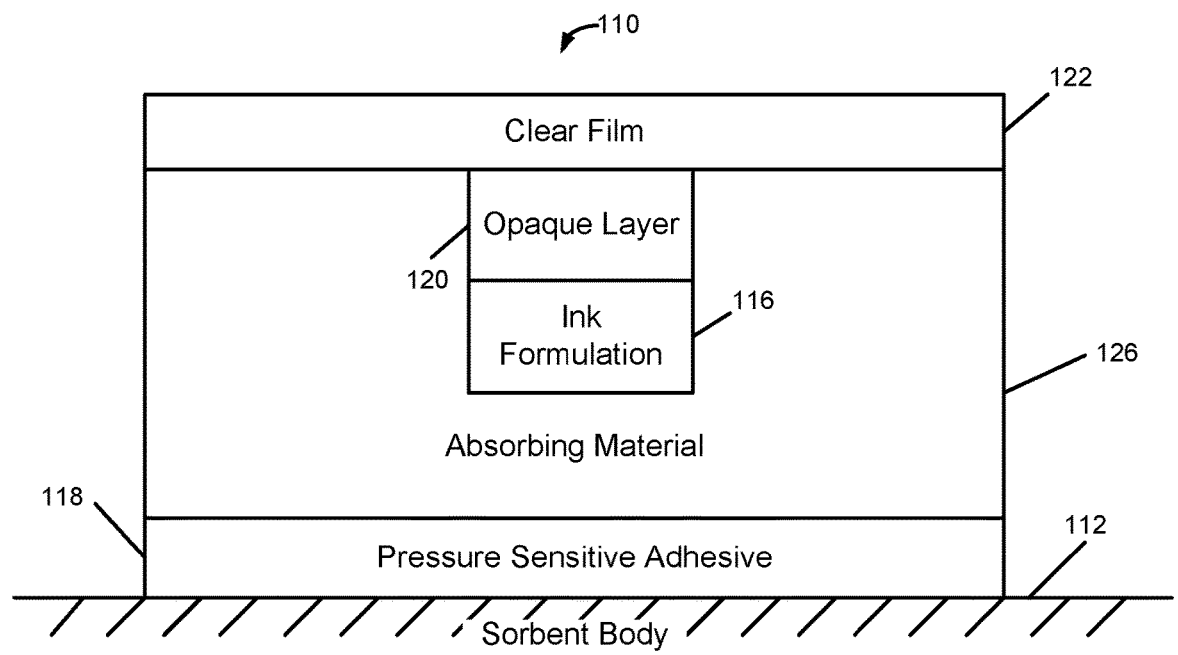
FIG. 2A is a third embodiment of a saturation indicator in contact with a sorbent body in which the saturation indicator includes an absorbing material.

Referring to FIG. 2A, another embodiment of a saturation indicator 110 is shown. In comparison to the views illustrated in FIGS. 1A and 1B of the first embodiment, the saturation indicator 110 further includes an absorbing material 126 configured to support the universal indicating ink formulation 120 and to absorb a sorbate that has ingressed from the edges of the saturation indicator 110 from the sorbent body 112. The absorbing material 126 may facilitate transport of the sorbate from the sorbent body 112 to the universal indicating ink formulation 116. The resin of the universal indicating ink formulation 116, being soluble in the sorbate, dissolves upon contact with the sorbent, allowing for a dye-sorbate solution to disperse within the absorbing material 126 that becomes viewable from the top through the clear film 122. The PSA 118 is configured to bond the absorbing material 126 to the sorbent body 112 and may provide a non-permeable barrier as previously indicated.

The absorbing material 126 can be made of a material such as MBPP which can absorb both hydrophobic and hydrophilic materials. However, it is also contemplated that the absorbing material 126 may be made of one or more of paper, hygroscopic material, acetobacteria, cotton wool, minerals, wood, or a polymer.

Figure 2B:
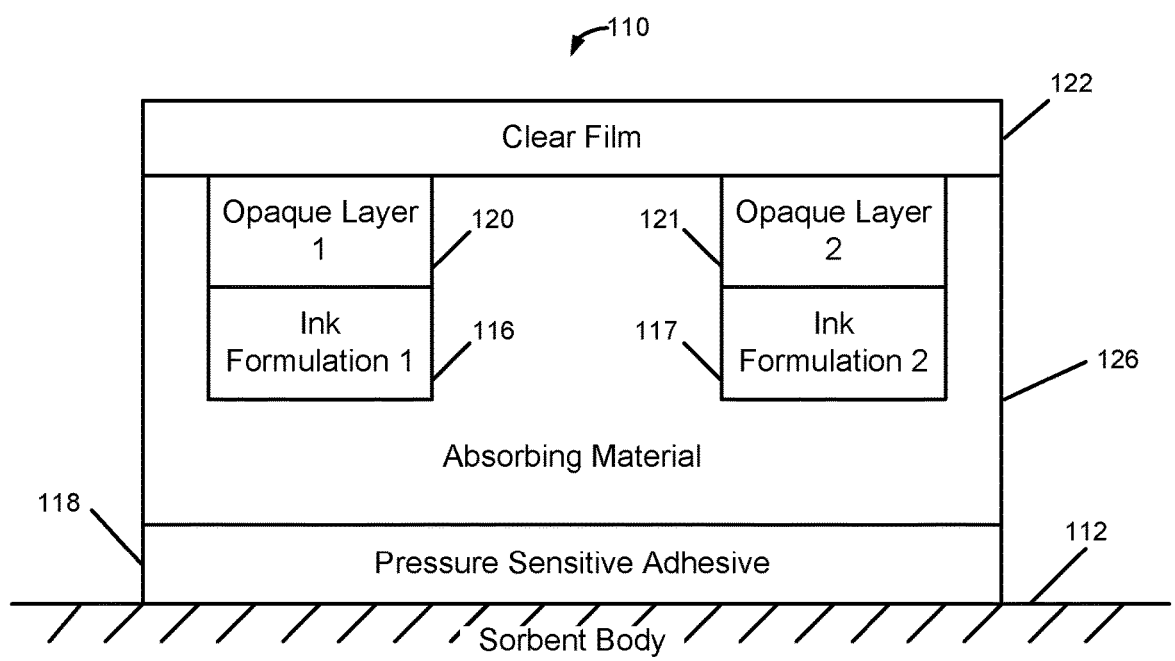
FIG. 2B is a fourth embodiment of a saturation indicator in contact with a sorbent body in which the saturation indicator includes an absorbing material and has multiple ink formulations.

In some forms, a second indicating ink formulation 117 and a second opaque layer 121 can additionally be disposed within the absorbing material 126, as shown in FIG. 2B. As noted previously, a second indicating ink formulation 117 can be used to indicate an additional solvent or solvents in addition to those that can be indicated using the first indicating ink formulation 116. Again, the dye in this second indicating ink formulation 117 can be soluble within an applied sorbate such that it may become viewable through the clear film 122 for indication. For example, the ink formulation 116 may be soluble in either hydrophobic or hydrophilic sorbates, such that a color-change in the absorbing material 126 is evinced when the ink formulation 116 is dissolved by a hydrophobic or hydrophilic sorbate. The second ink formulation 117 may be soluble in an alternative or tertiary sorbate, for example a neutral solvent or an amphipathic or amphiphilic solvent. In some forms, an alternative color-change in the absorbing material 126 may be presented when the ink formulation 117 is dissolved by a neutral sorbate, allowing for the user to visually determine the sorbate which has been absorbed by the sorbent body 112.

Some material constructions and chemical formulations are now described to provide better detail of the system. These examples are intended to be illustrative but not limiting.

In one form, the opacity layer includes a white pigment and polyacrylate resin. This composition may be purchased from Fuji Film North America Corporation, Graphic Systems Division of Kansas City, Kans. as Fujifilm 850-311 Opaque White. Other cross-linkable resins containing a dispersed pigment could also be used. Such resins are not limited to a UV-curable or cross-linkable opacity layer, but could include another layer whose purpose is primarily to cover over the ink indicating layer(s). The indicating ink may include acrylic resin (Joncryl® 67 available from BASF of Charlotte, N.C.) and the dye. The resin is not limited to acrylic resin, but the resin should allow for a stable dispersion of the dye within the resin. Other examples of resin include, but are not limited to, polyesters, rubbers, latexes, silicones, styrene copolymers and urethanes, and mixtures thereof. The choice of dye can be significant because some dyes are soluble in only hydrophilic liquids, while other dyes are selectively soluble in other types of solvents. In this one preferred formula, Koch Red 2214 (identified as Acid Red 1) and Solvent Red 7335 (identified as Solvent Red 24) available from Robert Koch Industries, Inc. of Bennett, Colo. (for example) are used for hydrophilic soluble and hydrophobic soluble inks, respectively. Those are only exemplary dyes and are not limiting, but the dyes should be soluble in the solvents that are to be indicated by the saturation indicator. Some examples of other dyes include, but are not limited to, anthracene, azo, anthraquinone, pyrazolone, quinine dye, and mixtures thereof. If the label is intended to indicate using hydrophilic solvents, then the dye should be soluble in hydrophilic liquids. Similarly, for indicating against hydrophobic liquids the dye should be soluble in hydrophobic liquids. Therefore all colors can be utilized as long as they perform in the same manner as the dyes specified above.

In one particular formulation, the hydrophilic ink formulation can include 22 parts Acid Red 1 as a pigment dispersed in 7 parts Joncryl® 67. These components are dispersed in 47 parts n-propanol and 26 parts water. The target formulation has a pigment to binder ratio of 3:1. The oil indicating ink was adapted from this formula. It was found that the same resin system (Joncryl® 67, 7 parts) will function as a carrier for the hydrophobic dye (Solvent Red 24) as well, effectively creating a universal ink indicating formula. N-propanol, 71 parts, is used to solubilize the resin and disperse the ink. While we chose to suspend the dyes, we were also successful in creating suspensions of the dyes, but our coat weights were lower and can work but will involve more machine passes to achieve the same final coating thickness. Other resins were also evaluated, including different acrylate resins, styrene-isoprene copolymers, and other rubber based resins. It was found that Joncryl® 67 worked well in n-propanol and a wide range of other solvents, and presented good rheological characteristics.

Figure 3:
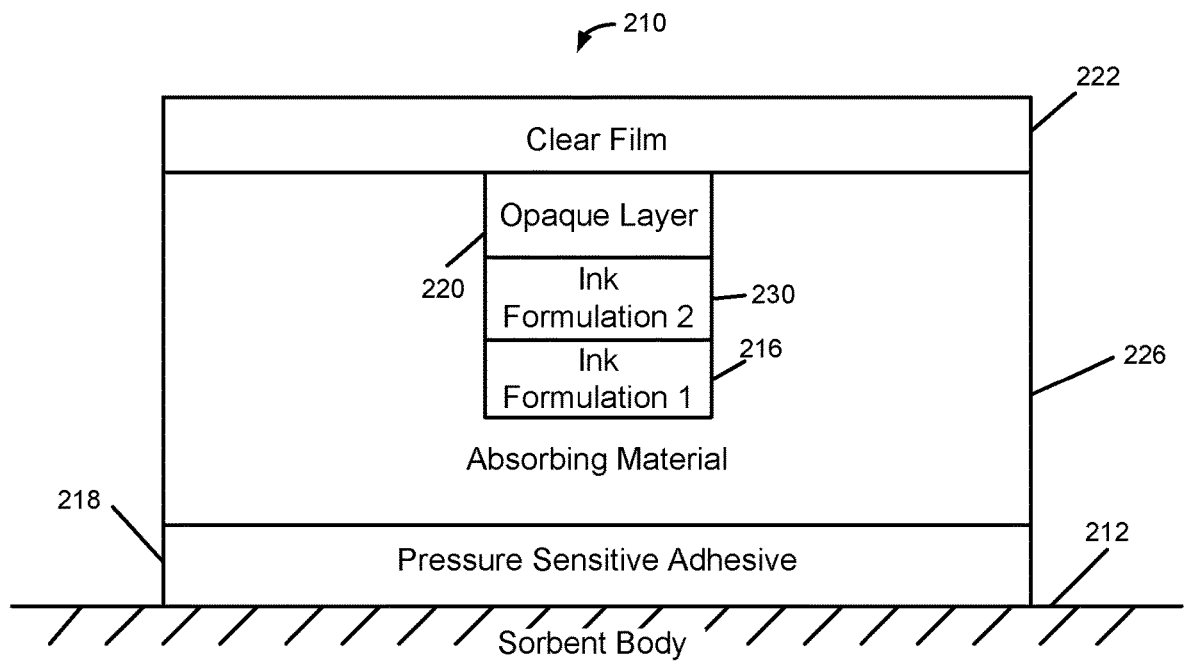
FIG. 3 is a fifth embodiment of a saturation indicator in contact with a sorbent body in which the saturation indicator has a universal ink indicating formulation and a second ink indicating formulation.

A further embodiment of the saturation indicator 210 is shown in FIG. 3 in which the first and second ink formulations 216 and 230 are stacked upon one another beneath the opaque layer 220. In this way, only a single opaque layer 220 may be used to initially shield both ink formulations 216 and 230 from view. However, both ink formulations 216 and 230 are still dissolvable for indication when they are contacted by the corresponding sorbate(s).

Figure 4:
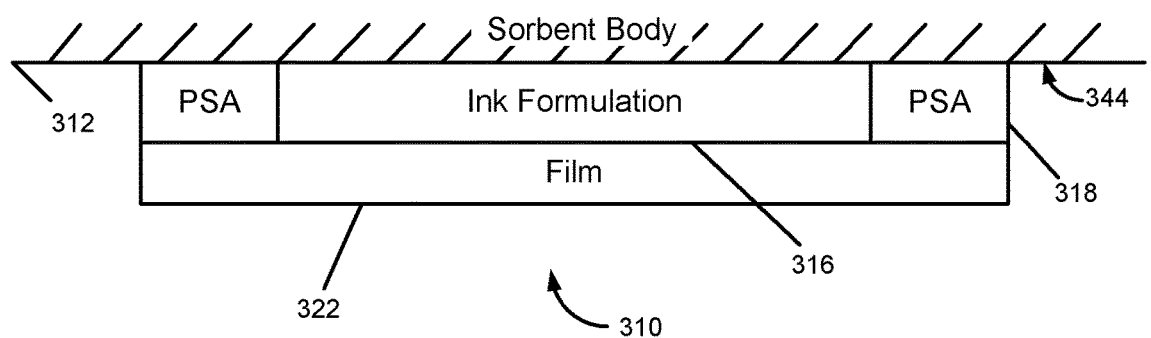
FIG. 4 is a sixth embodiment of a saturation indicator in which the saturation indicator is attached to the bottom side of a sorbent body to accommodate an upward migration of ink to provide a color change in the sorbent body itself.

In still another embodiment, as shown in FIG. 4, a saturation indicator 310 may be configured to be placed on the lower surface 344 of the sorbent body 312. As illustrated, the PSA 318 bonds the saturation indicator 310 to the lower surface 344 of the sorbent body 312 and, more specifically, bonds the film 322 (clear or otherwise) to the sorbent body 312. The PSA 318 may be disposed around a periphery of the saturation indicator 310 such that the universal indicating ink formulation 316, which is primarily supported by the film 322, is in contact with the sorbent body 312.

With this arrangement of the ink formulation 316, a sorbate absorbed by the sorbent body 312 may flow directly into the universal indicating ink formulation 316 and the released dye can migrate through the sorbent body 312 to an upper surface for viewing by a user. More specifically, the sorbate may be absorbed through the top surface 342 of the sorbent body 312 and flow to the lower surface 344 of the sorbent body 312. The sorbate may then reach the lower surface 344 of the sorbent body 312 and contact the universal indicating ink formulation 316 and create a dye-sorbate solution. This dye-sorbate solution migrates from the lower surface 344 of the sorbent body 312 to the upper surface 342 of the sorbent body 312, causing a color change or indication on the top surface of the sorbent body 312. The extent of the color change may be indicative of the degree of saturation of the sorbent body 312.

In an alternative embodiment, the sorbent body 12 may include a color-changing cover sheet disposed on the upper surface of the sorbent body. The color-changing cover sheet may be made of color forming materials, leuco dyes, pH sensitive materials, solvent sensitive materials, swellable elements, and the like. The sorbate is configured to saturate the underlying sorbent body 12, and to spread throughout the sorbent body and through the interface between the sorbent body and the color-changing cover sheet. When the sorbate contacts the color-changing cover sheet, the color-changing cover sheet changes color to indicate that a predetermined threshold of saturation has occurred in the sorbent body 12.

In some forms, a cover sheet may be employed to indicate the state of absorption of the sorbent body 12. A chemical interaction between the cover sheet and the sorbate may cause the dissolving cover sheet to dissolve, indicating that the predetermined threshold of saturation has been met. When the cover sheet dissolves, an underlying graphic indicator may become visible, thereby providing visual indication that the sorbent body 12 has reached its predetermined threshold of saturation.

In a modified form, a dissolving chemical may be supported by the sorbent body 12 and initially separated from the cover sheet. Upon partial or full saturation of the sorbent body 12, the dissolving chemical is capable of migrating through the sorbent body 12 to the dissolving cover sheet in order to react with the dissolving cover sheet. The dissolving cover sheet may be made of voided materials with micro-air bubbles, stress whitening fibers, ion-exchange resins for color forming, and the like.

In an additional alternative, the cover sheet may be reactive with the sorbate or a chemical made able to migrate to the cover sheet by virtue of the saturation of the sorbate into the sorbent body 12. The cover sheet may become clear by reaction, thereby revealing an underlying graphic pattern.

In another embodiment, the sorbent body 12 is layered, having a non-colored layer and a colored layer. It is possible for the non-colored layer and the colored layer to be made of the same or different materials. The sorbate may be configured to saturate both the non-colored layer and the colored layer. Saturation of the colored layer may cause the colored layer to exhibit a color change, the color change being a different color than the non-colored layer and indicating saturation of the sorbent body 12. The colored layer may be visually viewable to a user from an upper side, a lower side, or an edge side of the colored layer. It is possible for multiple non-colored layers and colored layers to be disposed within the sorbent body 12.

It is further contemplated that a color-changing mechanism can be configured to show either a local saturation on the sorbent body or an overall saturation of the sorbent body 12.

It is possible for the sorbent body 12 to indicate local saturation. For example, a plurality of graphic patterns may be placed on a surface of the sorbent body 12. Thus, when the sorbate contacts an area of the surface of the sorbent body 12, a graphic in the associated area may become visible or smeared, indicating that the associated area has been saturated. Indication of local saturation may allow the user to determine which areas are unused to allow for reposition of the sorbent body for the further absorption.

In some embodiments a physical change in the sorbent body occurs after the sorbent body 12 has reached the predetermined saturation threshold. For example, the sorbent body 12 may be configured to swell upon saturation. It is also possible for the sorbent body 12 to include an inner layer of material disposed between two outer layers. The inner layer may be configured to swell or shrink upon saturation, transitioning from a first volume to a second volume. The inner layer which has fully transitioned from the first volume to the second volume may indicate a fully saturated inner layer. A viewing window may be integrated within the outer layers to show the position of the inner layer. For example, a portion of the inner layer may be made of a colored material. As the inner layer swells or shrinks, the colored portion transitions out of the viewing window, disappearing when the sorbent body reaches the predetermined saturation threshold. As an alternative, the color or indicator may initially be external to the viewing window and progress into the window as the volume of the inner layer transitions.

Figure 5:
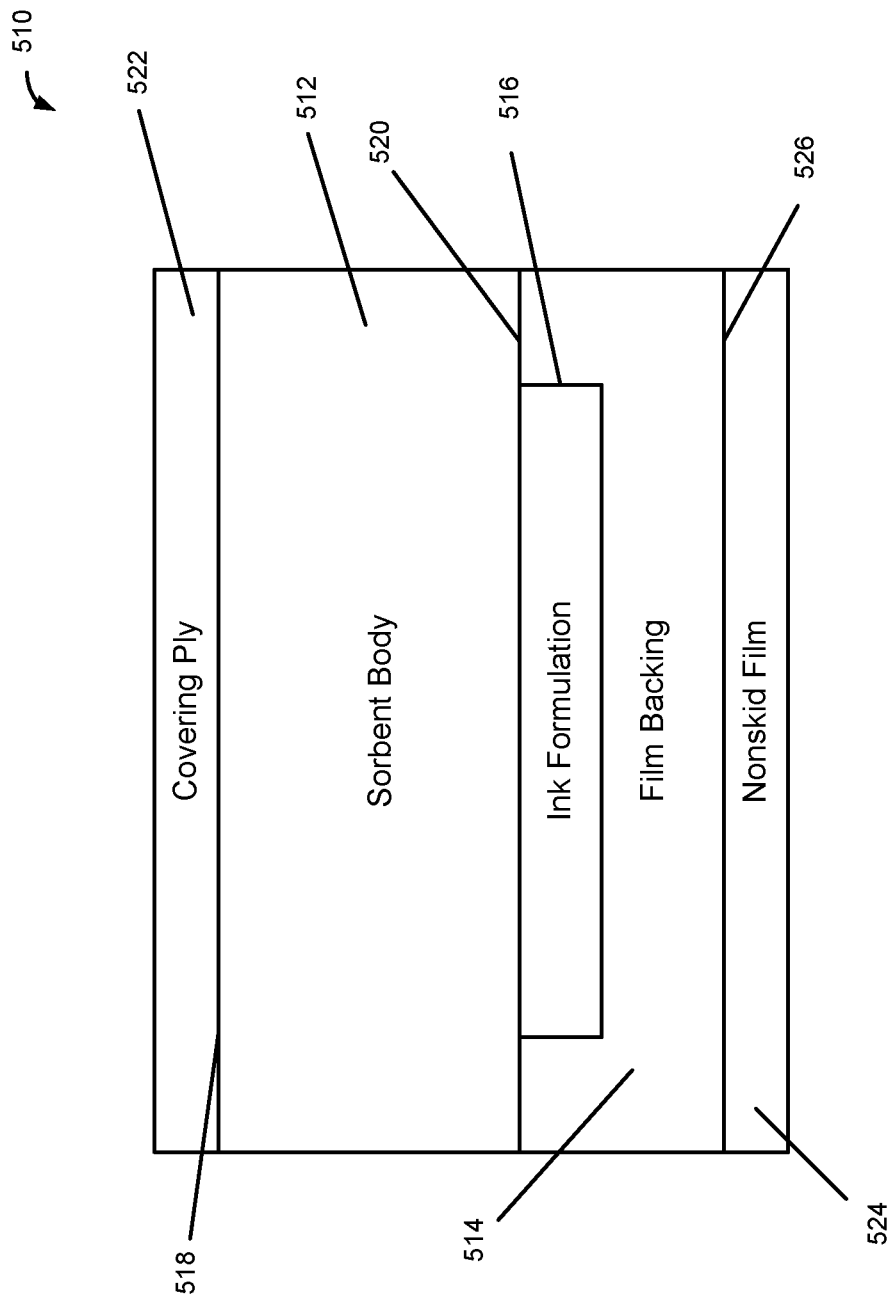
FIG. 5 is a schematic illustration of a saturation indication system according to a seventh embodiment in which the film backing is integrated into the sorbent body by ultrasonic welding in an irreversible fashion.

Referring now to FIG. 5, a saturation indication system 510 is shown unlike the first six illustrated embodiments in that it does not involve a label or attachable tag, but rather the indicator components are irreversibly bonded to the sorbent body during construction using ultrasonic welding or the like. Despite the difference in the manner of attachment and construction, some similar components are found in that the saturation indication system 510 includes a sorbent body 512, a film backing 514, and a universal indicating ink formulation 516.

The sorbent body 512 includes an upper surface 518 and a lower surface 520, and is again configured to absorb a sorbate. In some instances, the sorbent body 512 can be a sorbent pad formed by meltblown polypropylene. In other instances, the sorbent body 512 can comprise pads of various other sorbent materials such as those discussed above. The sorbent body 512 can further include a covering ply 522 coupled to the upper surface 518 of the sorbent body 512. The covering ply 522 may improve performance and mechanical properties of the upper surface 518 if desired for a given application. For example, in some instances the covering ply 522 can have a rough upper surface to aid in traction atop the sorbent body 512. In some other instances the covering ply 522 can have a smooth upper surface to reduce traction atop the sorbent body 512. In yet other instances the covering ply 522 can have different textural properties as desired or help to provide a level of rigidity to the sorbent body 512.

The film backing 514 is irreversibly bonded to the lower surface 520 of the sorbent body 512. In some instances, the film backing 514 can comprise a spunbond polypropylene material that is ultrasonically welded to the sorbent body 512 which is absorbent of the sorbate in a manner similar, if not identical to, the sorbent body 512. The film backing 514 covers at least a portion of a surface area of the lower surface 520 of the sorbent body 512. However, in other instances, such as in the depiction in FIG. 5, the film backing 514 can be extended to cover the entire surface area of the lower surface 520.

Additionally, the film backing 514 may include a nonskid film 524 coupled to a bottom surface 526 of the film backing 514, opposite the sorbent body 512. The nonskid film 524 is configured to provide a non-permeable barrier, which inhibits transport of the sorbate through the non-permeable barrier. The nonskid film 524 is also configured to provide a tractive surface to the bottom of the film backing 514.

The film backing 514 is further coated with the universal indicating ink formulation 516 over a portion thereof, which is then at least partially supported by the film backing 514.

The universal indicating ink formulation 516 may therefore be disposed partially within the film backing 514, as well as being coated onto the film backing 514 between the film backing 514 and the sorbent body 512. The universal indicating ink formulation 516 includes a resin and a dye dispersed in the resin, similar to the universal ink formulations 116, 216, 316 described above.

In some instances, the universal indicating ink formulation 516 can contain various combinations of dye resin, and can further comprise various other materials. For example, in some instances, the universal indicating ink formulation 516 can include 20 parts dye and 10 parts resin, and can additionally contain 68.4 parts solvent, and 1.6 parts additive. The dye can, for example, comprise 10 parts Red 2214 and 10 parts Red 7335. The resin can, for example, be Dianal BR-53, a styrene acrylic copolymer. The 68.4 parts of solvent can, for example, comprise 34.2 parts n-butyl acetate and 34.2 parts toluene. The 1.6 parts additive can, for example, be DisperBYK 108 from BYK Chemie, a hydroxyl functional carboxylic acid ester.

The dye and the resin of the universal indicating ink formulation 516 are again soluble when exposed to a sorbate from the sorbent body 512. Similarly, the sorbent body 512 is configured to absorb the sorbate and, when the sorbent body 512 is saturated to at least a pre-determined threshold, some amount of sorbate will be introduced to the film backing 514 and the ink formulation 516 found between the film backing 514 and the sorbent body 512.

The sorbate absorbed by the sorbent body 512 can be selected from the group of categories of sorbates consisting of hydrophobic sorbates, hydrophilic sorbates, neutral sorbates, and amphiphilic sorbates. The universal indicating ink formulation 516, including both they dye and the resin, is configured to be soluble in a plurality of sorbates selected from the aforementioned group of sorbates.

Prior to contact with the solvent or sorbate, the dye of the universal indicating ink formulation 516 is initially stationary within the resin before the sorbate flows from the sorbent body 512 (and possibly through the film backing 514 in part as well) into contact with the universal indicating ink formulation 516. Once the dye is dissolved in the sorbate, the dye is released, and migrates into and through the sorbent body 512 to the upper surface 518 for viewing by a user. This thereby indicates that the pad has passed a threshold point of saturation, requiring replacement.

More specifically, in use, the sorbate may be absorbed through the upper surface 518 of the sorbent body 512 and flow to the lower surface 520 of the sorbent body 512. The sorbate may then reach the lower surface 520 of the sorbent body 512 and directly contact the ink formulation 516 from the tip and also flow into the film backing 514 for additional contact with the universal indicating ink formulation 516 from the sides and bottom, thereby creating a dye-sorbate solution. This dye-sorbate solution can then migrate back through the lower surface 520 of the sorbent body 512 to the upper surface 518 of the sorbent body 512, causing a color change or indication on the upper surface 518. This dispersion of the dye to the upper surface 518 is indicative that the resin has been contacted by the sorbate. The extent of the color change may be indicative of the degree of saturation of the sorbent body 512.

It should be appreciated that, in the illustrated embodiment, the sorbent body 512 effectively forms an opaque layer disposed above the universal indicating ink formulation 516, and is configured to conceal the universal indicating ink formulation 516 before the dye is dispersed into the sorbent body 512.

It is to be noted that the various indicators described herein could be potentially used separately or in combination with one another. Further, these indicators could potentially be used with other indicators not expressly described herein.

It will be understood that various modifications may be made to the embodiments disclosed herein. Therefore, the above description should not be construed as limiting, but merely as exemplifications of preferred embodiments. Those skilled in the art will envision other modifications within the scope, spirit and intent of the invention.

What is claimed is:

1. A saturation indication system comprising:
a sorbent body having an upper surface and a lower surface and being configured to absorb a sorbate;
a film backing being irreversibly bonded to the lower surface of the sorbent body; and
a universal indicating ink formulation partially coated onto the film backing such that the universal indicating ink formulation is disposed between the film backing and the sorbent body, the universal indicating ink formulation including:
a resin, and
a dye dispersed in the resin, the dye is configured to indicate a state of saturation of the sorbent body, wherein the universal indicating ink formulation is soluble in two or more of hydrophobic sorbates, hydrophilic sorbates, neutral sorbates, and amphiphilic sorbates.

2. The saturation indication system of claim 1, wherein the dye is stationary within the resin before the sorbate saturates the resin of the universal indicating ink formulation, wherein the dye disperses into the sorbent body after the sorbate saturates the resin, and wherein dispersion of the dye is indicative that the resin has been contacted by the sorbate.

3. The saturation indication system of claim 1, wherein the sorbent body is a meltblown polypropylene sorbent pad and the film is a spunbond polypropylene film integrated into the meltblown polypropylene sorbent pad.

4. The saturation indication system of claim 3, wherein the spunbond polypropylene film is integrated into the meltblown polypropylene sorbent pad by bonding them together via ultrasonic welding.

5. The saturation indication system of claim 1, further comprising a covering ply coupled to one of the upper surface and the lower surface of the sorbent body, opposite the film backing.

6. The saturation indication system of claim 5, wherein the covering ply is a spunbond polypropylene layer ultrasonically welded to the upper surface of the sorbent body.

7. The saturation indication system of claim 1, further comprising a nonskid film coupled to the film backing, opposite the sorbent body.

8. The saturation indication system of claim 7, wherein the nonskid film provides a non-permeable barrier inhibiting transport of the sorbate through the non-permeable barrier.

9. The saturation indication system of claim 1, wherein the film backing covers a portion of a surface area of the lower surface of the sorbent body.

10. The saturation indication system of claim 1, wherein the resin is made of at least one of acrylic, polyesters, rubbers, latexes, silicones, and styrene copolymers.

11. The saturation indication system of claim 1, wherein the dye is at least one of anthracene, azo, anthraquinone, pyrazolone, and quinine dye.

12. The saturation indication system of claim 1, wherein the resin is opaque.

13. The saturation indication system of claim 1, wherein the sorbent body forms an opaque layer disposed above the universal indicating ink formulation and configured to conceal the universal indicating ink formulation before the dye is dispersed into the sorbent body.

14. The saturation indication system of claim 1, wherein the universal indicating ink formulation contains 20 parts dye, 10 parts resin, 68.4 parts solvent, and 1.6 parts additive.

15. The saturation indication system of claim 14, wherein:
the 20 parts dye includes 10 parts Red 2214 (Acid Red 1) and 10 parts Red 7335 (Solvent Red 24);
the resin includes a styrene acrylic copolymer;
the 68.4 parts of solvent includes 34.2 parts n-butyl acetate and 34.2 parts toluene; and
the 1.6 parts additive is a hydroxyl functional carboxylic acid ester.

16. A saturation indication system comprising:
a sorbent body having an upper surface and a lower surface and being configured to absorb a sorbate;
a film backing being irreversibly bonded to the lower surface of the sorbent body; and
a universal indicating ink formulation partially coated onto the film backing such that the universal indicating ink formulation is disposed between the film backing and the sorbent body, the universal indicating ink formulation including:
a resin, and
a first dye and a second dye dispersed in the resin, the first dye and the second dye being configured to indicate a state of saturation of the sorbent body,
wherein the universal indicating ink formulation is soluble in hydrophobic sorbates and hydrophilic sorbates.

17. The saturation indication system of claim 16, wherein the first dye is soluble in hydrophilic sorbates and wherein the second dye is soluble in hydrophobic sorbates.

18. The saturation indication system of claim 16, wherein the universal indicating ink formulation is soluble in amphiphilic sorbates.

19. The saturation indication system of claim 16, wherein the first dye is Red 2214 (Acid Red 1), the second dye is Red 7335 (Solvent Red 24), and the resin includes a styrene acrylic copolymer.

20. The saturation indication system of claim 16, wherein the universal indicating ink formulation includes equal parts of the first dye and the second dye.

* * * * *